United States Patent
Tonetti

Patent Number: 5,795,592
Date of Patent: Aug. 18, 1998

[54] PHARMACEUTICAL COMPOSITION TO ENHANCE TISSUE HEALING AND REGENERATION AND APPLICATION KIT COMPRISING IT

[76] Inventor: Maurizio Tonetti, The Procter & Gamble Company, 11450 Grooms Rd., Cincinnati, Ohio 45242-1434

[21] Appl. No.: 587,600

[22] Filed: Jan. 2, 1996

Related U.S. Application Data

[62] Division of Ser. No. 130,958, Oct. 4, 1993, abandoned.

[51] Int. Cl.$^6$ ............................................. A61K 9/14
[52] U.S. Cl. ..................... 424/484; 424/422; 424/423; 424/435
[58] Field of Search ................... 422/422–428, 422/484–389; 514/772, 772.1, 773, 781.1

[56] References Cited

U.S. PATENT DOCUMENTS

| | | | |
|---|---|---|---|
| 4,175,326 | 11/1979 | Goodson | 433/80 |
| 4,250,163 | 2/1981 | Nagai et al. | 424/14 |
| 4,454,110 | 6/1984 | Caslavsk et al. | 424/54 |
| 4,569,837 | 2/1986 | Suzuke et al. | 424/28 |
| 4,685,883 | 8/1987 | Jernberg | 433/215 |
| 4,764,377 | 8/1988 | Goodson | 424/435 |
| 4,788,062 | 11/1988 | Gale et al. | 424/449 |
| 4,789,662 | 12/1988 | Thomas-Leurquin et al. | 514/21 |
| 5,047,244 | 9/1991 | Sanvordeker et al. | 424/435 |
| 5,059,123 | 10/1991 | Jernberg | 433/215 |
| 5,130,121 | 7/1992 | Kopolow et al. | 424/47 |
| 5,266,326 | 11/1993 | Barry et al. | 424/423 |
| 5,290,552 | 3/1994 | Sierra et al. | 424/94.64 |
| 5,318,780 | 6/1994 | Viegas et al. | 424/427 |

FOREIGN PATENT DOCUMENTS

| 315112 | 4/1983 | Japan. |
|---|---|---|
| 84-315112/51 | 4/1983 | Japan. |

OTHER PUBLICATIONS

151 USPQ, pp. 185–191.In re Walles, Tousignant, and Houtman.

*Primary Examiner*—Gollamudi S. Kishore
*Attorney, Agent, or Firm*—Douglas C. Mohl; Betty J. Zea; Jacobus C. Rasser

[57] ABSTRACT

Compositions comprising a calcium channel blocker as an active agent and a biocompatible carrier for fixing the agent temporarily at the site of application, or precursor compounds forming such a biocompatible carrier "in situ".

It is useful for the treatment of a body site to enhance tissue healing and regeneration, particularly in dental medicine and in surgery.

4 Claims, 3 Drawing Sheets

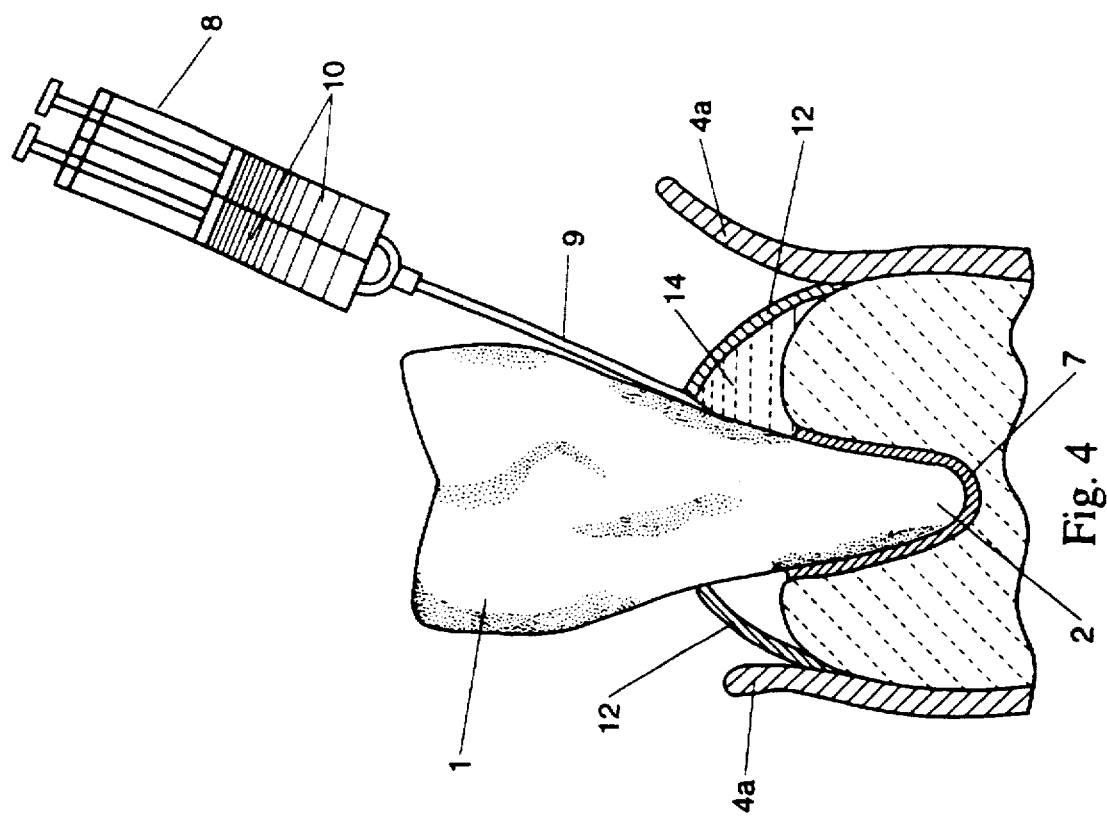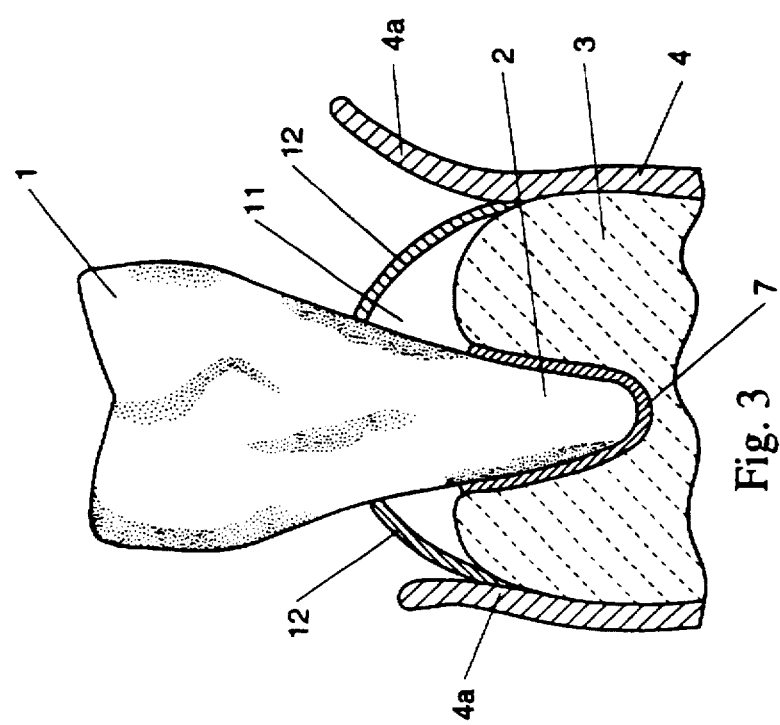

PHARMACEUTICAL COMPOSITION TO ENHANCE TISSUE HEALING AND REGENERATION AND APPLICATION KIT COMPRISING IT

This is a division of application Ser. No. 08/130,958, filed on Oct. 4, 1993 now abandoned.

TECHNICAL FIELD

The present invention is related to a pharmaceutical composition comprising a calcium channel blocker and a biocompatible carrier, preferably a polymer being useful for the initiation and promotion of the regeneration of tissue and bone material after diseases or surgical operation. The invention also concerns a special kit comprising the pharmaceutical composition, a delivery device, an applicator and film material for covering the treated site.

BACKGROUND OF THE INVENTION

Following diseases and/or surgical intervention human and other animal tissues heal by replacement with a fibrotic scar tissue. Such tissue does not generally possess the functional characteristics of the original tissue. Various attempts have therefore been made to obtain a healing response characterized by regeneration, i.e. the replacement of lost tissue with a newly generated tissue functionally and morphologically similar to the original one. Regeneration of lost tissue has been successfully obtained in selected clinical situations by the exclusion in the repopulation of the wound of undesirable tissues by means of mechanical barriers. Such process has been termed guided tissue regeneration.

In defined clinical situations both natural healing responses and guided tissue regeneration procedures present several limitations which decrease the extent and predictability of the desired healing outcome. Clinical application of the concept of guided tissue regeneration in periodontics (treatment of gum diseases), implantology (replacement of lost teeth by artificial bone anchored ones), orthopedics, plastic surgery, etc. has proven to be highly effective in selected conditions characterized by a particular topographic configuration of the tissue to be regenerated. In most situations, however, results are less satisfactory both in terms of amounts of obtained regenerated tissue and their predictability. Classical explanations of this phenomenon have centered the attention upon limits arising from insufficient recruitment of specific progenitor cells. Locally delivered growth factors with chemotactic and proliferative effects have thus been proposed as a means to overcome the observed limitations. Further recognition that a space must be maintained within the wound to allow for blood clot stabilization has led to the engineering of stiffer mechanical barriers both resorbable and non resorbable.

From a critical analysis of the results obtained applying the principles of guided tissue regeneration to both periodontal and extra oral sites, at least one other interpretation was found for the insufficient and unpredictable regeneration observed: an insufficient perfusion of the blood clot during its initial colonization by granulation tissue and insufficient perfusion of the newly formed tissue itself. Such relative hypoperfusion can be thought to result in impairment of production of cytokines, growth factors and other messengers responsible for the transduction of wound healing and regenerative signals.

The concept of guided tissue regeneration of humans has been known for about 10 years, and it was shown that this biological concept is applicable to regeneration of periodontal tissues lost due to periodontitis. Several limitations have also been recognized. Among these, particular emphasis has been placed on the fact that only certain defect morphotypes predictably heal with a clinically significant regeneration. Generally, the healing of infrabony defects or class II furcation defects is considered to be the most favorable. This has been explained in terms of presence of a space to allow for stabilization and organization of the blood supply. A third important aspect is the possibility of nutrition of the blood clot and newly regenerated tissue, i.e., the microvascular blood supply.

The invention as claimed makes use of the above knowledge and provides a pharmaceutical composition adapted to the use in guided tissue regeneration. The composition comprises a calcium channel blocker as an active agent and a biocompatible carrier for fixing the agent temporarily at the site of application. The invention also comprises an application kit for the administration of the pharmaceutical composition as claimed, comprising a calcium channel blocker and a biocompatible carrier or precursor compounds thereof wherein the said components are comprised in a multichamber applicator for mixing the agent and the carrier before administration.

The present invention specifically enables the functional limitations in blood supply that may negatively affect the extent and predictability of regeneration to be overcome when "unfavorable" clinical situations are selected. In this respect different pharmacological agents were selected which have the following known characteristics: a) Increase microvascular blood flow; b) increase microvascular endothelium proliferation; c) protect tissues from ischemia and reperfusion damages. A typical example of a suitable agent is the calcium channel blocker nifedipine which was selected on the basis of the possible presence of a "periodontal thropism" of its effects as suggested by the induction of gingival hyperplasia. Further, nifedipine is a very safe drug currently used to treat hypertension, angina and Raynaud's disease. To avoid the systemic effects, a local delivery system was devised whose vehicle has been shown not to negatively affect periodontal regeneration. The delivery composition can be used in combination with or without physical barriers such as plastic or resorbable polymer films. Specific formulations and application technique must be adapted to the different applications.

Other suitable calcium channel blockers for use in the present invention include diltiazem, verapamil, nicardipine, gallopamil, iradipine, nimodipine, fendilin, prenylamin, amlodipine basylate, flodipine and bepridil. Salts of these agents such as the hydrochloride salt are also acceptable for use. The level of calcium channel blocker useful in the present invention is generally from about 0.001% to about 50%, preferably from about 0.01% to about 10% by weight of the total composition.

A preferred material for use in the present invention is human fibrin. This material has unique application in the present invention due to its clotting capabilities. Polymers of various types are also useful in the present invention and include those polymer materials which are safe for use in the oral cavity and wounds of a human or lower animal. Such polymers are known, including for example polymers and copolymers such as polylactic acid ("PLA"), polyglycolic acid ("PLG"), poly lactyl-co-glycolic acid ("PLGA"), polyaminoacids such as polyaspartame, chitosan, collagen, polyalburrin, gelatin and hydrolyzed animal protein, polyvinyl pyrrolidone xanthan and other water soluble gums, polyanhydride, and poly orthoesters. Preferred are polymers and copolymers of polylactic acid ("PLA"), polyglycolic acid ("PLG"), and poly lactylco-glycolic acid ("PLGA").

A preferred polymer useful for the present invention are the copolymers containing mixtures of lactide and glycolide monomers. Lactide monomeric species preferably comprise from about 15% to about 85%, most preferably from about 35% to about 65% of the polymers, while glycolide monomeric species comprise from about 15% to about 85% of the polymer, preferably from about 35% to about 65% on a molar basis. The molecular weight of the copolymer typically lies in the range of from about 1000 to about 120,000 (number average). These polymers are described in detail in U.S. Pat. No. 4,443,430, Apr. 17, 1984, to Mattei incorporated herein by reference in its entirety.

A feature of fluid gel or paste-like compositions containing certain of such copolymers is their transformation into near solid phase in the presence of aqueous fluid such as water, aqueous buffers, serum, crevicular fluid, or other body fluid. For example, when a sample of such a gel is placed into a tube containing water or human serum, the composition becomes nearly solid in the receptor phase. This is believed to be due to insolubility of the poly(lactyl-co-glycolide) copolymer in water, and related aqueous solvents such as may be present in wound or crevicular fluid. Thus, even though such fluid compositions can potentially be used advantageously when desired from a syringe-like apparatus, they still offer the advantages of solid devices at the treatment sites. Further, since such polymeric materials do undergo slow degradation via hydrolysis, the drug continues to release in a sustained manner from such compositions and the composition does not need to be surgically removed following tissue regeneration.

The polymer or human fibrin generally comprises from about 1% to about 90%, preferably from about 10% to about 70%, of the compositions/devices useful for the methods of the present invention. Generally, for the most preferred copolymers containing lactide and glycolide, less polymer is necessary as the amount of lactide goes up.

A BRIEF DESCRIPTION OF THE DRAWINGS

The invention is described in the present specification with reference to the enclosed drawings relating to an application example in the dental field which is only used for explaining the present invention, but without restricting the described invention in any way.

FIG. 3 shows the same view with a positioned expanded Teflon® film before the application of a nifedipine composition according to the invention;

FIG. 4 shows the situation during the application of the nifedipine composition;

EXAMPLE

Delivery Composition

Figure 2:
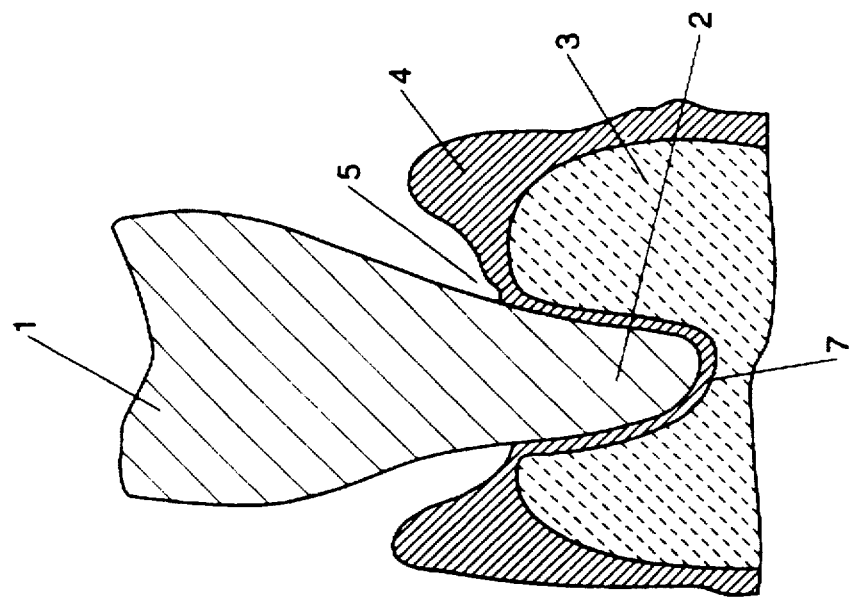
FIG. 2 shows a sectional view of the defect, section along line I—I of FIG. 1.

A composition for the local delivery to be applied within the periodontal wound was prepared. Such delivery composition consisted of two different drug reservoirs of the active agent nifedipine dispersed within a human fibrin vehicle. Once placed into the wound the active agent of the delivery composition is slowly resorbed during the wound healing process to result in a sustained local release of the medication.

A first drug reservoir consisting of a nifedipine solution in the vehicle was incorporated to assure a high rate of delivery in the very early phases. Since nifedipine is a relatively water insoluble agent, micronized drug particles were used as the major drug reservoir. The micronized particles were finely dispersed into the final fibrin clot. This served as the long term delivery platform. As the fibrin clot will be removed during the wound healing process (over a period of 2–3 days) some particles will be exposed to a higher regional tissue fluid flow, thus sequentially increasing their rate of delivery through solvation of the microparticle.

The delivery composition consisted of 50 μg/ml of nifedipine in solution, 500 μg/ml of nifedipine micronized particles (particle size between 6 and 8 μm) interspersed within a fibrin clot obtained converting 35 mg/ml of human fibrinogen with 250 international units (I.U.) of thrombin in the presence of 20 mM calcium chloride ($CaCl_2$) (e.g., "Tisseel" of the manufacturer Immuno AG, Osterreichisches Institut fur Immunoderivate, Vienna AT). The rate of resorption of the delivery composition was decreased by incorporation of 1.5 trypsin inhibitor units (TIU/ml) of the protease inhibitor aprotinin.

The delivery composition was aseptically prepared as follows from pharmaceutical grade reagents. Two separate components were prepared to be mixed at the site of application.

Component A:

1000 μg of nifedipine microparticles were added to 500 I.U. of lyophilized thrombin and stored at 4° C. until use. Shortly before use the thrombin and the nifedipine particles were suspended in I ml of distilled water and injection with 40 mM $CaCl_2$ in solution. Thrombin, being water soluble, was completely dissolved in water while the relatively water insoluble nifedipine particles were dispersed in a fine and homogeneous emulsion which was heated at 37° C.

Component B:

A solution containing 100 μg/ml of nifedipine was prepared in distilled water for injection containing 5% ethanol (v/v, final concentration) shortly before use. To this solution 3 TIU/ml of lyophilized purified aprotinin were added. 1 ml of the nifedipine-aprotinin solution was used to solvate 70 mg of human fibrinogen at 37° C. under gentle stirring.

Component A and Component B were mixed at a 1:1 ratio (v:v) during administration of the preparation into the space surgically created in the periodontal wound to obtain polymerization of the delivery composition "in situ" as described in the application example. The two solutions were administered using a manifold syringe.

Application Example

Figure 1:
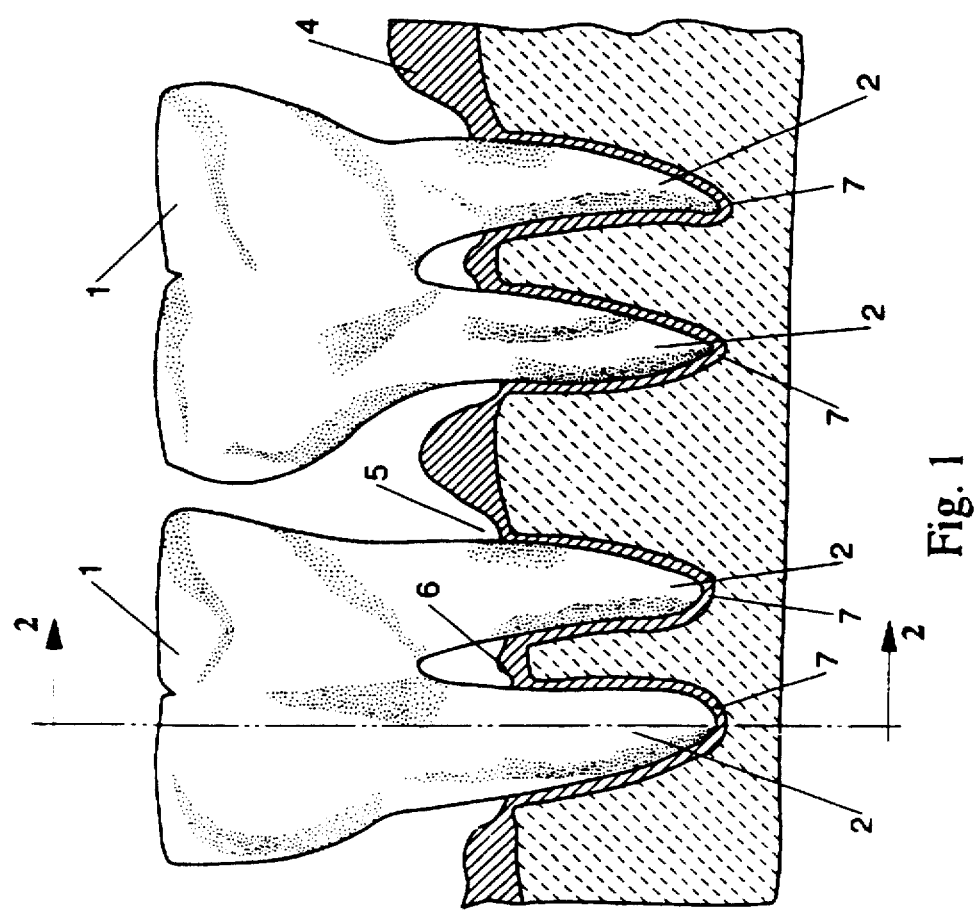
FIG. 1 shows the appearance of a defect of the gum and the bone around the teeth in a buccal view.

An application example is illustrated in the field of periodontology to overcome the limits of conventional GTR techniques in obtaining regeneration of tooth support lost to periodontal disease in unfavorable situations (FIG. 1, 2). In this application the delivery composition is placed during surgical intervention in combination with a barrier membrane to enhance regeneration according to the principles of GTR (FIG. 3).

Predictability of tissue regeneration according to GTR is dependent upon careful selection of periodontal defects with specific morphological characteristics: 3 wall and/or 2 wall infra bony defects or Class II furcation involvements. In most situations such as class III furcation involvements. 1 wall infra bony defects or supra bony defects GTR procedures are highly unpredictable. Reasons for such limitation have been reviewed.

After gaining surgical access to the defect, removal of granulation tissue, careful scaling and root planing of infected root surfaces and visualization of the defect according to accepted practice for GTR, expanded poly-tetrafluoro. ethylene (e-PTFE) barrier membrane(s) 12 (Gore periodontal material, W. L. Gore and Associates, Flagstaff Ariz.) were placed to create a space 11 between the root 2 of the tooth 1, the alveolar bone 3 and the gingival tissue (see FIG. 3). The membrane 12 was carefully placed to exactly limit the area of tissue loss to be regenerated and to cover sound alveolar bone 3 for 2–3 mm in every direction. The space 11 created under the membrane 12 was then filled by injecting the delivery composition 10 with a manifold syringe 8 (FIG. 4). The needle 9 was passed between the collar of the membrane 12 and the root 2 of the tooth 1. Extreme care was employed to assure complete fill of the defect delimited by the membrane 12 with the delivery composition 14. After application the delivery composition polymerized "in situ" within a few seconds (FIG. 4). Following completion of the positioning of the delivery composition 14, membrane(s) 12 were checked in terms of exact adaptation with the alveolar bone 3 and the root 2 of the tooth 1, and thus ensure exclusion of gingival connective tissue and epithelium from gaining access to the wound. The e-PTFE membrane 12 limiting the delivery composition 14 was then covered with the mucoperiosteal flaps which were coronally repositioned to completely cover the membrane(s) (see FIG. 5). The subject was then instructed in terms of post-operative home care according to accepted surgical practice.

Figure 6:
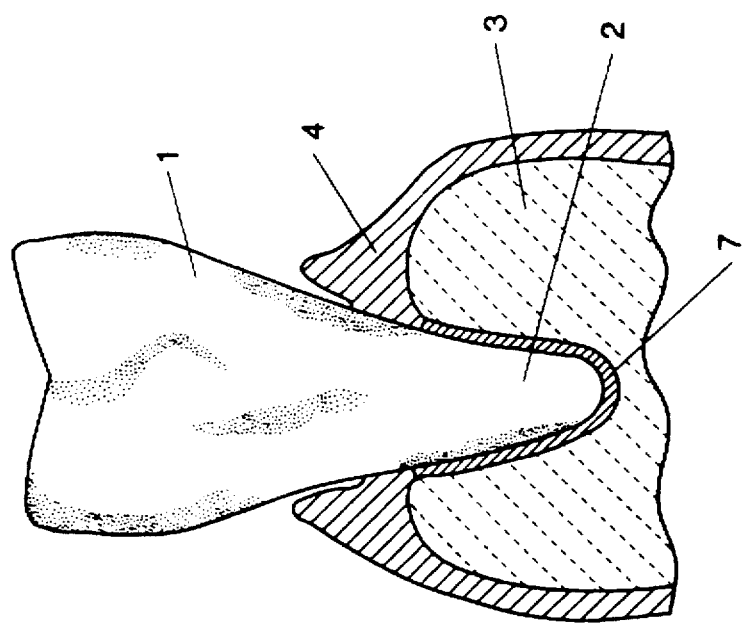
FIG. 6 illustrates the obtained clinical result at the end of the healing process.

A second operation was performed four weeks later to remove the membrane(s). At that time the amount of regenerated soft tissue was visualeed. The regenerated tissue completely filled the space surgically created under the membrane (FIG. 6). Such soft tissue has been shown to result from repopulation of the wound area by adjacent periodontal ligament and alveolar bone tissue and has been shown to gain the morphological and functional characteristics of periodontal ligament and alveolar bone following a period of tissue maturation during completion of the regenerative healing response. The regenerated soft tissue was then carefully covered with the partial thickness mucoperiosteal flaps according to standard surgical procedures.

The healing response was then monitored over time by:
a) clinical probing attachment level (PAL); i.e. a point related to the most coronal extension of the periodontal ligament as measured with a periodontal probe with a millimeter scale from a fixed anatomical landmark: the cemento-enamel junction;
b) changes in radiographic density, i.e., a change in tissue radiographic density mostly dependent upon changes in calcium content in the tissue and thus upon changes in tissue mineralization as measured by computer assisted densitometric image analysis (CADIA) of standardized identical radiographs.

The clinical outcome of a representative case treated with local application of the nifedipine delivery composition in combination with barrier membranes is briefly described with reference to the enclosed drawings.

FIGS. 1 and 2: In a tooth 1 with a hopeless prognosis based upon extreme tooth mobility deriving from loss of periodontal support, the presence of a class III through and through furcation and two deep 1 wall defects (mean PAL loss 11 mm) a gain of PAL of almost 6 mm was observed. As shown in the buccal view of FIG. 1 as well as in the sectional view of FIG. 2 the support of the root 2 in the bone 3 was poor, the ligament 7 and the gum 4 was retrogressive and periodontal pockets 5 were formed.

FIG. 3: The position of the barrier membrane 12 before provisional closure of the coronal flaps 4a is shown generally: After removing the granulation tissue the infected site 5, 6 around the tooth 1 is covered by a barrier membrane 12 from e-PFTE. The membrane is attached with a thread 13.

Subsequently as shown in FIG. 4 the components 10 of the pharmaceutical compositions are introduced by the multichamber syringe 8. The components 10 are mixed shortly before entering into the injection needle 8. The mixed composition 14 penetrates into the space 11 between the membrane 12, the alveolar bone 3 and the root 2 of the tooth 1. Here the composition coagulates and is then able to release the active agent over time.

Figure 5:
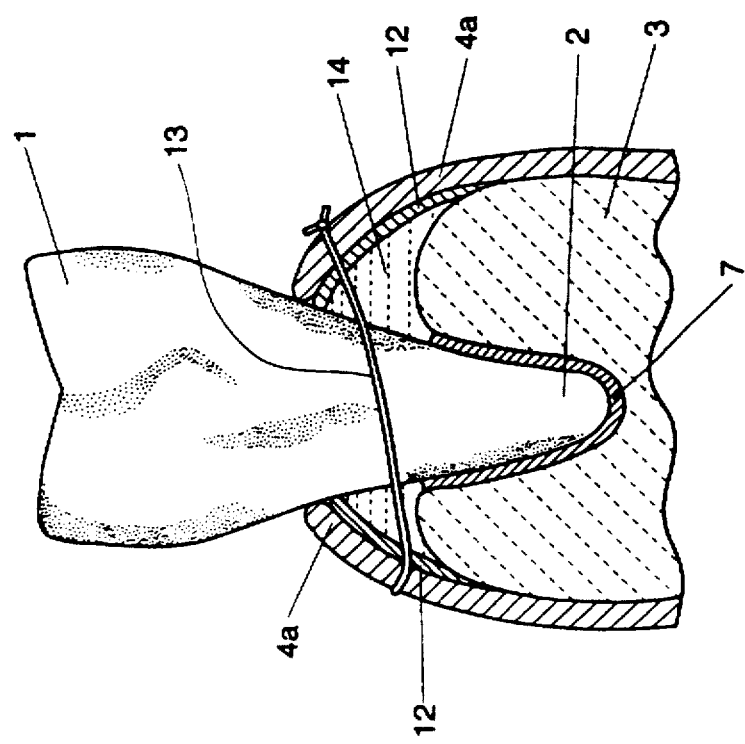
FIG. 5 shows the view after closure of the mucoperiosteal flaps which cover the membrane.

FIG. 5 shows the situation during the first period of the healing process when the barrier membrane is in position, covered by the mucoperiosteal flaps 4a.

FIG. 6 shows the progress of the regeneration of the tissue after the removal of the membrane, with coronal flap reposition (normally the membrane is removed about 4 to 6 weeks after beginning of the treatment).

Few months after the beginning of the treatment the furcation was completely closed as determined by clinical probing, thus indicating regeneration of periodontal ligament. A radiographic net intensity gain of more than 150 CADIA values was observed both in the furcation area and in the 1 wall defects indicating regeneration of mineralized bone tissue. As a result of both periodontal ligament and alveolar bone regeneration the tooth had gained normal stability at 6 months.

What is claimed is:

1. A process for the treatment of a body site to enhance the tissue healing and regeneration comprising the following steps:
   a) gaining access to the body site;
   b) limiting the area of tissue loss, with creation of a space, with or without use of a barrier membrane, at the area of the tissue loss; and
   c) placing a pharmaceutical composition comprising a calcium channel blocker as an active agent and a biocompatible carrier for fixing the agent temporarily at the site of application into the space and filling it, said biocompatible carrier is selected from the group consisting of fibrin, a polyamino acid, gelatin, polylactide, glucuronic and polymer, polylactide glycolide copolymer and polyvinylpyrrolidone.

2. A process according to claim 1, wherein the calcium channel blocker is selected from the group consisting of nifedipine, gallopamil, verapamil, diltiazem, fendilin and prenylamin.

3. A process according to claim 1, wherein the calcium channel blocker is comprised in a solution or suspension for immediate release, and additionally it is comprised as a component in dispersed degradable particles forming a delivery device for a delayed release of the agent.

4. A process according to claim 1 which comprises the compounds for preparing the following components immediately before use:

Component A: suspension of microparticles of nifedipine and lyophilized thrombin in water comprising a calcium ion source.

Component B: solution of nifedipine in water comprising a solvent as ethanol, lyophilized aprotinin and human fibrinogen and placing components A and B at the site of application into the space and filling it.

* * * * *